US00PP28369P3

(12) United States Plant Patent
Finn

(10) Patent No.: US PP28,369 P3
(45) Date of Patent: Sep. 12, 2017

(54) BLACKBERRY PLANT NAMED 'COLUMBIA GIANT'

(50) Latin Name: ***Rubus* subg. *Rubus* Watson**
Varietal Denomination: Columbia Giant

(71) Applicant: The United States of America, as represented by the Secretary of Agriculture, Washington, DC (US)

(72) Inventor: Chad E. Finn, Corvallis, OR (US)

(73) Assignee: THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 24 days.

(21) Appl. No.: 14/756,637

(22) Filed: Sep. 28, 2015

(65) Prior Publication Data

US 2017/0094856 P1 Mar. 30, 2017

(51) Int. Cl.
*A01H 5/08* (2006.01)

(52) U.S. Cl.
USPC ..... Plt./203

(58) Field of Classification Search
USPC ..... Plt./230, 203
See application file for complete search history.

*Primary Examiner* — June Hwu
(74) *Attorney, Agent, or Firm* — Gail Poulos; John D. Fado

(57) ABSTRACT

A new and distinct blackberry cultivar that originated from seed produced from a cross between the female blackberry plant 'NZ 9629-1' (unpatented) and the male parent blackberry plant 'ORUS 1350-2' (unpatented). This new blackberry cultivar can be distinguished by its high yields of extremely large and very uniformly shaped berries with very good firmness, color, and flavor and that are borne on vigorous, completely thornless trailing plants.

4 Drawing Sheets

Latin name of the genus and species of the plant claimed: 'COLUMBIA GIANT' is a blackberry plant that is *Rubus* subg. *Rubus* Watson.

Variety denomination: The new blackberry plant claimed is of the variety denominated 'Columbia Giant' *Rubus* subg. *Rubus* Watson.

BACKGROUND OF THE INVENTION

The present invention relates to a new and distinct blackberry cultivar designated 'Columbia Giant' and botanically known as *Rubus* subg. *Rubus* Watson. This new blackberry cultivar was discovered in Corvallis, Oreg. in July 2008 and originated from a cross between the female blackberry plant 'NZ 9629-1' (unpatented) and the male parent blackberry plant 'ORUS 1350-2' (unpatented). 'Columbia Giant''s spinelessness is derived from 'Lincoln Logan' (unpatented) that can be found as a parent four and five generations back in 'Columbia Giant''s pedigree. 'Columbia Giant' was selected from the same population as 'Columbia Star' (U.S. Plant patent application Ser. No. 13/815,074, now U.S. Plant Pat. No. 25,532). The original seedling of the new cultivar was asexually propagated at a nursery in Benton County, Oreg. The new cultivar was established in vitro from a cane cutting and microcuttings have been taken and rooted from this sort of culture. The present invention has been found to be stable and to reproduce true to type through successive asexual propagations.

BRIEF DESCRIPTION OF THE PHOTOGRAPHS

This new blackberry plant is illustrated by the accompanying photographs that show the fruit of the plant and machine harvested fruit, as well as canes and entire plants; the colors shown are as true as can be reasonably obtained by conventional photographic procedures.

Figure 1:
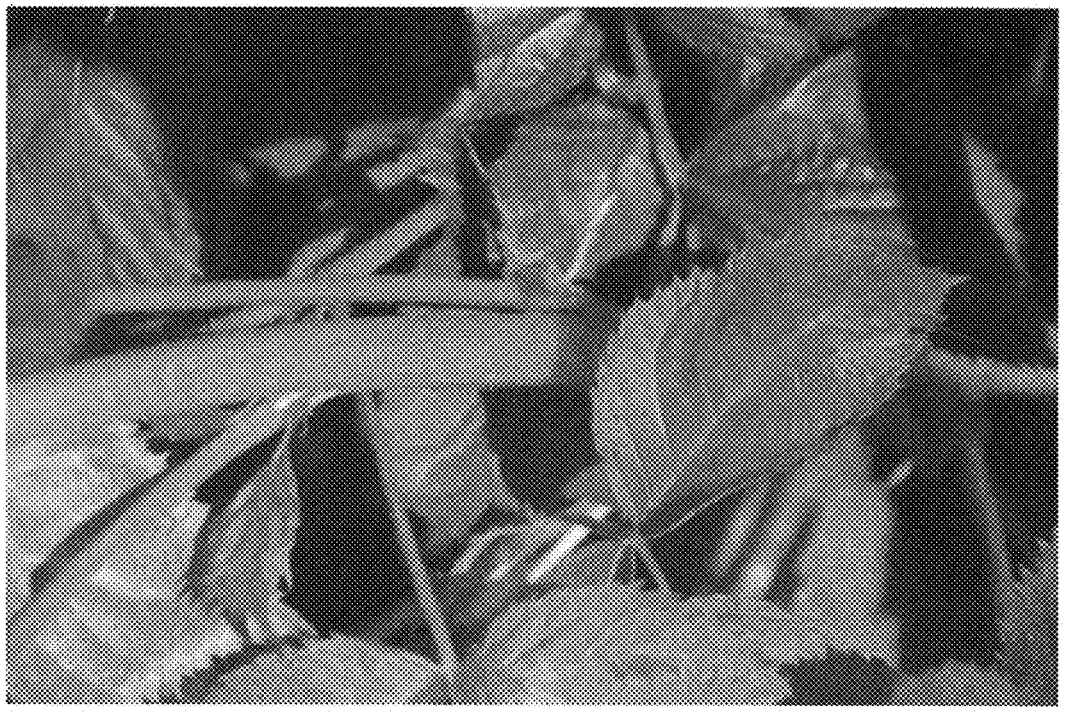

FIG. 1. shows a section of a spineless primocane and a leaf.

Figure 2:
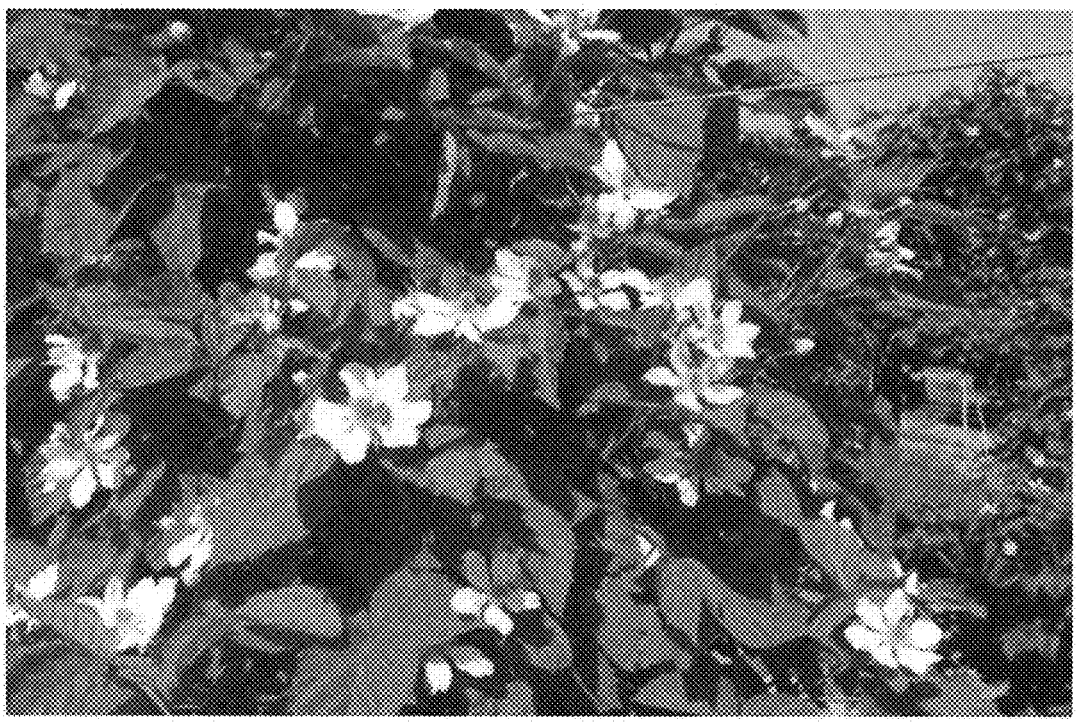

FIG. 2. shows flowers on the plant. As is typical for commercial production, trailing primocanes are lifted from the ground in late summer and tied to a two wire trellis with the lower wire approximately 1.0 m above the ground and the upper wire approximately 1.5 m above the ground.

Figure 3:
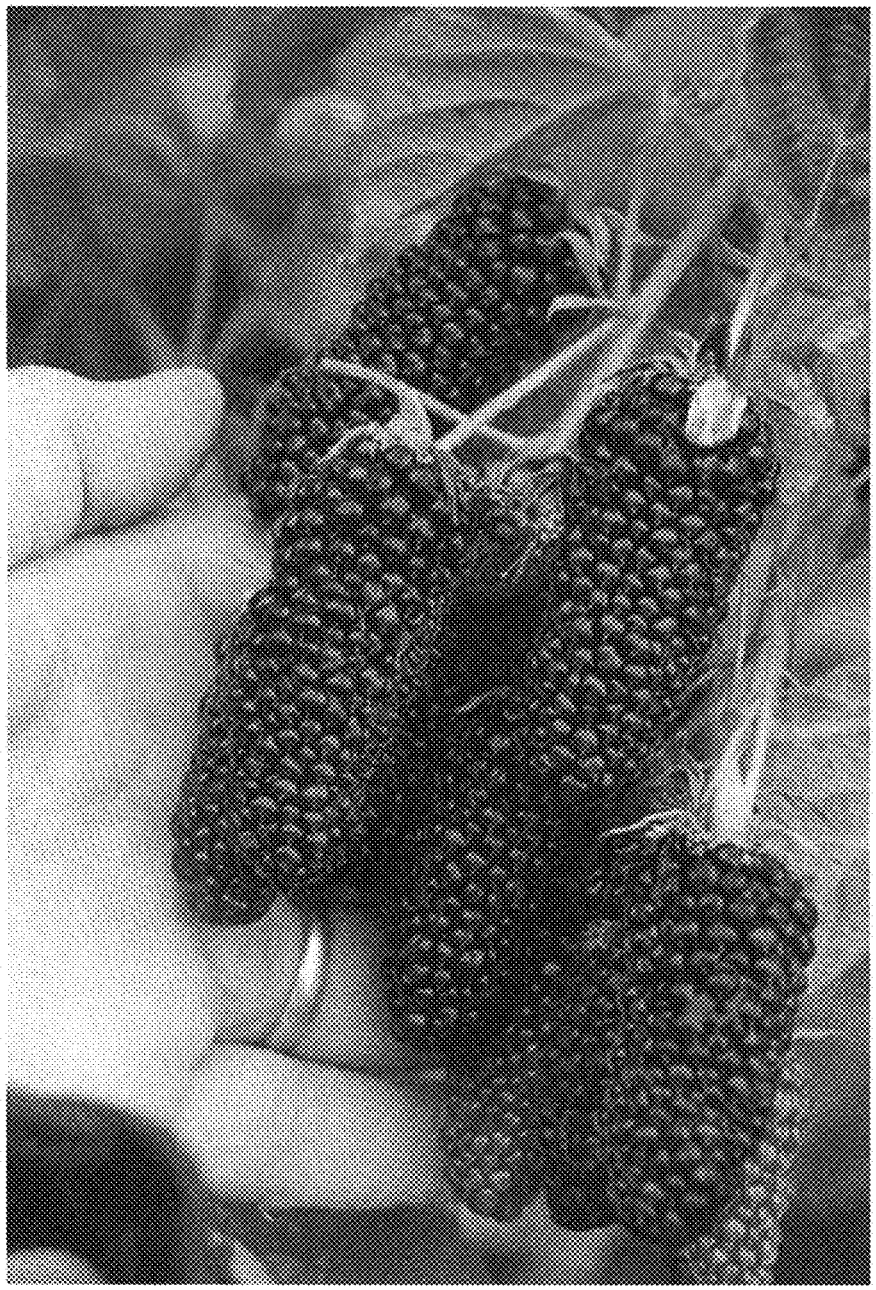

FIG. 3. shows typical fruit in a fruit cluster in the field.

Figure 4:
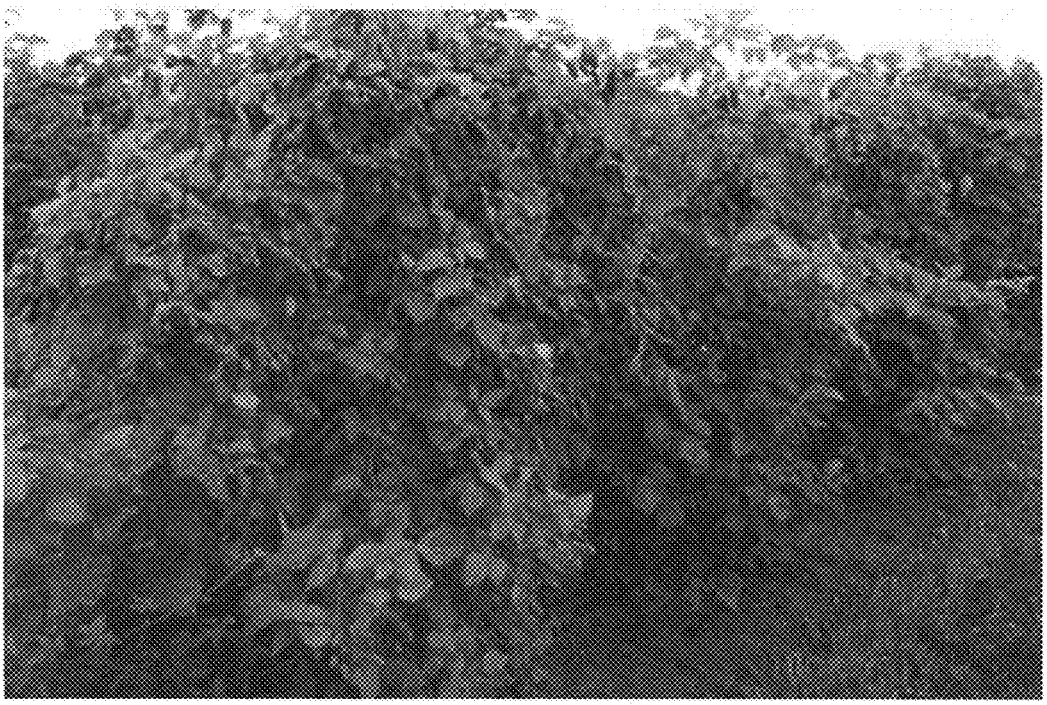

FIG. 4. shows an entire 4-year old plant. As is typical for commercial production, trailing primocanes are lifted from the ground in late summer and tied to a two wire trellis with the lower wire approximately 1.0 m above the ground and the upper wire approximately 1.5 m above the ground.

DETAILED DESCRIPTION OF THE NEW VARIETY

The following description of 'Columbia Giant' is based on observations taken from 2011 to 2014 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Columbia Giant' has not been observed under all possible environmental conditions. Color terminology follows The Royal Horticultural Society Colour Chart. London (R.H.S.) ($5^{th}$ edition, 2007).

Table 1 shows plant characteristics of the new cultivar. Characteristics include plant vigor growth habit, date of budbreak, timing of primocane emergence, winter tolerance in Aurora, Oreg. (45° 16' 49" N/122° 44' 50" W), and winter tolerance in Lynden, Wash. (48° 56' 48" N/122° 27' 2" W).

TABLE 1

Plant Characteristics of 'Columbia Giant'.

| Characteristic | Columbia Giant |
|---|---|
| Plant vigor | High compared to Black Diamond |
| Growth habit | Trailing |
| Date of budbreak | 27 March |
| Timing of primocane emergence | Early to medium compared to Black Diamond |
| Winter tolerance in Aurora, Oregon (45° 16' 49" N/122° 44' 50" W) | Very good-excellent (better than Marion) |
| Winter tolerance in Lynden, Washington (48° 56' 48" N/122° 27' 2" W) | Good-very good (better than Marion) |

Table 2 shows floricane and mature primocane characteristics of the new cultivar. Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane color at terminus, floricane lateral length, floricane lateral strength, primocane color at base, primocane color at midpoint, primocane color at terminus, and floricane length (range).

TABLE 2

Floricane and Mature Primocane Characteristics of 'Columbia Giant'.

| Characteristic | Columbia Giant |
|---|---|
| Diameter at base | 1.17 cm |
| Diameter at midpoint | 0.84 cm |
| Diameter at terminus | 0.19 cm |
| Internode length at base | 3.35 cm |
| Internode length at midpoint | 6.32 cm |
| Internode length at terminus | 3.95 cm |
| Presence of spines further than 0.6 m from the soil surface | Absent |
| Presence of spines less than 0.6 m from the soil surface | Absent |
| Floricane color at base | 144A |
| Floricane color at midpoint | 144A |
| Floricane color at terminus | 144B |
| Floricane lateral length | Medium-long |
| Floricane lateral strength | Medium |
| Primocane color at base | 144A with overtones of 185B |
| Primocane color at midpoint | 144A |
| Primocane color at terminus | 146C |
| Floricane length (range) | 2.12-6.22 m |

Table 3 shows primocane foliage characteristics of the new cultivar. Primocane characteristics include mature compound leaf width, mature compound leaf length, number of leaflets per primocane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on primocane leaflet upper surface, pubescence on primocane leaflet undersurface, primocane leaf color abaxial, primocane leaf color adaxial, petiole length, petiole color: upper surface, petiole color: undersurface, petiolule length terminal leaflet, petiolule length first distal leaflet, petiolule color abaxial, petiolule color adaxial, stipule length, stipule width, and stipule attitude. Fruit is borne only on floricanes.

TABLE 3

Primocane Foliage Characteristics of 'Columbia Giant'.

| Characteristic | Columbia Giant |
|---|---|
| Mature compound leaf width | 21.70 cm |
| Mature compound leaf length | 18.50 cm |
| Number of leaflets per primocane compound leaf | Usually 5 |
| Mature leaflet shape | Ovate |
| Mature leaflet apex | Broadly acuminate |
| Mature leaflet base | Cordate |
| Mature terminal leaflet width | 8.47 cm |
| Mature terminal leaflet length | 11.88 cm |
| Mature first lateral leaflet width | 6.35 cm |
| Mature first lateral leaflet length | 10.53 cm |
| Leaflet margin | Double serrate |
| Leaflet serration teeth length | 0.31 cm |
| Leaflet serration teeth width at base | 0.28 cm |
| Spine presence on leaves | Absent |
| Pubescence on primocane leaflet: upper surface | Light |
| Pubescence on primocane leaflet: undersurface | Light |
| Primocane leaf color abaxial | 137C |
| Primocane leaf color adaxial | 148B |
| Petiole length | 8.68 cm |
| Petiole color: upper surface | 1440 with gradation to 177B |
| Petiole color: undersurface | 145A |
| Petiolule length: terminal leaflet | 2.61 cm |
| Petiolule length: first distal leaflet | 0.80 cm |
| Petiolule color: abaxial | 146B |
| Petiolule color: adaxial | 145A |
| Stipule length | 2.11 cm |
| Stipule width | 0.17 cm |
| Stipule attitude | Crossed near base and curled |

Table 4 shows floricane foliage characteristics of the new cultivar. Floricane characteristics include mature compound leaf width, mature compound leaf length, number of leaflets per floricane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, pubescence on floricane leaflet: upper surface, pubescence on floricane leaflet undersurface, floricane leaf color abaxial, floricane leaf color adaxial, petiole length, petiole color adaxial, petiole color abaxial, petiolule length terminal leaflet, petiolule length first distal leaflet, petiolule color abaxial, petiolule color adaxial, stipule length, and stipule width.

TABLE 4

Floricane Foliage Characteristics of 'Columbia Giant'.

| Characteristic | Columbia Giant |
|---|---|
| Mature compound leaf width | 16.67 cm |
| Mature compound leaf length | 9.81 cm |
| Number of leaflets per floricane compound leaf | Usually 3 |
| Mature leaflet shape | Ovate |
| Mature leaflet apex | Broadly acuminate |
| Mature leaflet base | Ovate |
| Mature terminal leaflet width | 5.30 cm |
| Mature terminal leaflet length | 7.85 cm |
| Mature first lateral leaflet width | 4.0 cm |
| Mature first lateral leaflet length | 6.55 cm |

TABLE 4-continued

Floricane Foliage Characteristics of 'Columbia Giant'.

| Characteristic | Columbia Giant |
|---|---|
| Leaflet margin | Double serrate |
| Leaflet serration teeth length | 0.28 cm |
| Leaflet serration teeth width at base | 0.39 cm |
| Pubescence on floricane leaflet: upper surface | Light |
| Pubescence on floricane leaflet: undersurface | Light |
| Floricane leaf color abaxial | 146B |
| Floricane leaf color adaxial | 147C |
| Petiole length | 7.22 cm |
| Petiole color adaxial | 144C |
| Petiole color abaxial | N144D |
| Petiolule length: terminal leaflet | 1.96 cm |
| Petiolule length: first distal leaflet | 0.26 cm |
| Petiolule color: abaxial | 144C |
| Petiolule color: adaxial | N144D |
| Stipule length | 1.04 cm |
| Stipule width | 0.09 cm |

Table 5 shows flower and flowering characteristics of the new cultivar. Flower and flowering characteristics include date 1st bloom, date full bloom, date last bloom, petal color, number flowers per cluster, number of petals per flower, flower diameter, petal length, petal width, number of sepals per flower, peduncle length, rachis length, peduncle color, and cyme type.

TABLE 5

Flower and Flowering Characteristics of 'Columbia Giant'.

| Characteristic | Columbia Giant |
|---|---|
| Date 1$^{st}$ bloom | 4 May |
| Date full bloom | 11 May |
| Date last bloom | 42145 |
| Petal color | 157C |
| Number flowers per cluster | 7.33 |
| Number of petals per flower | 5.83 |
| Flower diameter | 4.23 cm |
| Petal length | 1.43 cm |
| Petal width | 0.91 cm |
| Number of sepals per flower | 6.17 |
| Peduncle length (cm) | 25.69 cm |
| Rachis length (cm) | 9.08 cm |
| Peduncle color | 146B |
| Cyme type | Simple |

Table 6 shows fruit and fruiting characteristics of the new cultivar. Fruit and fruiting characteristics include date 5% of fruit were ripe, date 50% of fruit were ripe, date 95% of fruit were ripe, weight of primary fruit, weight of secondary fruit, weight of tertiary fruit, diameter of primary fruit at equator, diameter of 2° fruit at equator, diameter of 3° fruit at equator, diameter of 1° fruit at poles: tip, diameter of 1° fruit at poles: base, diameter of 2° fruit at poles: tip, diameter of 2° fruit at poles: base, diameter of 3° fruit at poles: tip, diameter of 3° fruit at poles: base, berry length primary fruit, berry length 2° fruit, berry length 3° fruit, ratio of primary fruit length to width, shape description, uniformity of berry shape, color when full ripe, number of drupelets per fruit, drupelet weight, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in brix), pH, titratable acidity (% as citric acid), and yield (actual kg·plt$^{-1}$).

TABLE 6

Fruit and Fruiting Characteristics of 'Columbia Giant'.

| Characteristic | Columbia Giant |
|---|---|
| Date 5% of fruit were ripe | 25 June |
| Date 50% of fruit were ripe | 5 July |
| Date 95% of fruit were ripe | 19 July |
| Weight of primary fruit | 14.07 g |
| Weight of secondary fruit | 13.27 g |
| Weight of tertiary fruit | 14.47 g |
| Diameter of primary fruit at equator | 2.14 cm |
| Diameter of 2° fruit at equator | 2.00 cm |
| Diameter of 3° fruit at equator | 1.97 cm |
| Diameter of 1° fruit at poles: tip | 1.17 cm |
| Diameter of 1° fruit at poles: base | 1.90 cm |
| Diameter of 2° fruit at poles: tip | 1.31 cm |
| Diameter of 2° fruit at poles: base | 2.08 cm |
| Diameter of 3° fruit at poles: tip | 1.32 cm |
| Diameter of 3° fruit at poles: base | 1.91 cm |
| Berry length primary fruit | 5.02 cm |
| Berry length 2° fruit | 4.67 cm |
| Berry length 3° fruit | 4.71 cm |
| Ratio of primary fruit length to width | 2.36 |
| Shape description | Long conic |
| Uniformity of berry shape | Excellent |
| Color when full ripe | Mostly 203B with N186C on ~5% drupelets |
| Number of drupelets per fruit | 181.70 |
| Drupelet weight | 77.0 mg |
| Individual seed weight | 26.9 mg |
| Glossiness | Medium glossy to dull |
| Firmness | Very good |
| Flavor | Very good |
| Texture of fruit when chewed | Excellent |
| Drupelet skin resistance to abrasion | Good |
| Ease of separation of fruit from pedicel | Easy |
| Machine harvestability | Excellent |
| Resistance to heat damage of fruit | Medium to good |
| Berries per inflorescence - mean | 7.00 |
| Berries per inflorescence range | 5-10 |
| Soluble solids (%; in Brix) | 11.25 |
| pH | 3.26 |
| Titratable acidity (% as citric acid) | 18.5 |
| Yield (actual kg · plt$^{-1}$) | 6.86 |
| Disease Response | Under a typical, minimal, disease management program does not exhibit any particular disease problems |

COMPARISON WITH PARENTAL AND COMMERCIAL VARIETIES

'Columbia Giant' differs from the female parent 'NZ 9629-1' (unpatented) in that 'Columbia Giant' has medium-sized, glossy, very large fruit (12-17 g), while 'NZ 9629-1' has slightly pubescent fruit that are smaller (4.5 g).

'Columbia Giant' differs from the male parent blackberry plant 'ORUS 1350-2' (unpatented) in that it is spineless, has conic berries with excellent flavor, while 'ORUS 1350-1' (unpatented) is spiny and has barrel shaped berries with poor flavor.

'Columbia Giant' differs from the commercial variety 'Marion' (unpatented) in that 'Columbia Giant' is spineless and has large yields of very large, firm, and very uniformly shaped fruit while 'Marion' is spiny and bears medium yields of medium sized, and soft fruit that are unevenly shaped. 'Columbia Giant' differs from the commercial variety 'Black Diamond' (unpatented) in that 'Columbia Giant' carries the 'Lincoln Logan' (unpatented) source of spinelessness and therefore the canes are completely spineless and the plants are vigorous with fruit that are very large and have excellent, aromatic flavor, while 'Black Diamond'

(unpatented) carries the 'Austin Thornless' (unpatented) source of spinelessness and so has spines on the base of the canes and the plants are not vigorous and they produce large fruit with a mild flavor. 'Columbia Giant' differs from the commercial variety 'Columbia Star' (U.S. Plant patent application Ser. No. 13/815,074, now U.S. Plant Pat. No. 25,532) based predominantly on a fruit size. 'Columbia Giant' fruit ranged from 12.2-16.3 g with mean primary fruit size of 14.1 g while 'Columbia Star' fruit ranged from 6.0-10.5 g with mean primary fruit size of 9.7 g.

The market use of Columbia Giant is primarily local fresh such as local farmers markets but it machine harvests well and processes well.

I claim:

1. A new and distinct cultivar of blackberry plant, substantially as illustrated and described, characterized by its high yields of extremely large and very uniformly shaped berries with very good firmness, color, and flavor and that are borne on vigorous, completely thornless trailing plants.

* * * * *